United States Patent [19]

Doumas et al.

[11] Patent Number: 4,563,429

[45] Date of Patent: Jan. 7, 1986

[54] BILIRUBIN ASSAY

[76] Inventors: Basil T. Doumas, 2430 Whipple Tree La., Brookfield, Wis. 53005; Kwok C. P. Poon, 2224 W. Wisconsin Ave. #211, Milwaukee, Wis. 53233

[21] Appl. No.: 453,492

[22] Filed: Dec. 27, 1982

[51] Int. Cl.$^4$ ............................................. G01N 33/72
[52] U.S. Cl. ....................................... 436/97; 436/903
[58] Field of Search ........................... 436/97, 175, 903; 422/61

[56] References Cited

PUBLICATIONS

Poon, Clinical Chemistry, 27 (4), 636–637, 1981.
Henry et al., "Clinical Chemistry-Principles and Technics", 2nd Ed., Harper and Row, New York, 1974, pp. 1045–1064.

*Primary Examiner*—Arnold Turk
*Attorney, Agent, or Firm*—Quarles & Brady

[57] ABSTRACT

An improved conjugated (direct) bilirubin assay comprises treating a sample to be assayed with a buffer having a pH of about 4 to 5 and containing iodide ions thereby decreasing the oxidation of hemoglobin to methemoglobin and preventing conjugated bilirubin from being oxidized to biliverdin. The iodide also prevents the destruction of the azopigment by the hemoglobin. The assay further comprises adding a diazo reagent to the treated sample, incubating the resulting mixture, adding ascorbic acid, alkaline tartrate and a caffeine reagent and then reading the absorbence at 600 nm. The concentration of direct bilirubin is calculated by comparison to the absorbance of unconjugated standard(s) analyzed by a method for total bilirubin. The improved assay is more accurate than prior art methods because hemoglobin interference is negligible. In a preferred embodiment the buffer is sodium acetate buffer having a pH of about 4.75 which contains 3 to 30 grams/L of potassium iodide. A kit containing the acetate buffer is also disclosed.

3 Claims, No Drawings

BILIRUBIN ASSAY

The present invention relates to a bilirubin assay. More particularly, it relates to a direct assay for bilirubin in which hemoglobin does not interfere with the results.

BACKGROUND OF THE INVENTION

Bilirubin is the principal pigment in blood serum and bile. It is derived from the porphyrin fraction of hemoglobin which is released by the disintegration of erythrocytes. Any disturbance that causes increased destruction of red blood cells results in an increase in bilirubin.

The determination of serum bilirubin is a necessary part of the routine evaluation of liver disease and the appearance of bilirubin in the urine can be the earliest sign of hepatobiliary disease.

A number of methods of assaying or quantitatively measuring bilirubin in the serum are based on the coupling of bilirubin with diazotized sulfanilic acid to form a red pigment in neutral solutions and a blue pigment in strongly acid or alkaline solutions. Van den Bergh and Snapper described the use of this color reaction for quantitative measurements of serum bilirubin in their article in Dent. Arch. Klin. Med. 110, 540–561 (1913). Later, Jendrassik and Grof combined caffeine-sodium benzoate with sodium acetate, diazotized sulfanilic acid, and formed the azobilirubin color within 10 minutes. Biochem. Z. 297, 81–89 (1938).

At the present time, the most commonly used method for measuring direct bilirubin is that proposed by Michaelsson which is based on the Jendrassik-Grof principle. Scand. J. Clin. Lab. Invest. 13, Suppl. 56, 1; (1960). In the Michaelsson method hydrochloric acid (HCl) is used to prevent unconjugated bilirubin from reacting; ascorbic acid is added to destroy the excess diazo reagent; and the caffeine reagent is added at the end to prevent overestimation of the direct bilirubin. The molar absorptivity of the alkaline azopigment is considerably higher in the absence of caffeine (about 12%) than in its presence, and since caffeine is needed for the reaction of the standard, it must also be added in the direct reaction.

In the Michaelsson method, even at a concentration as low as 0.6 g/L, hemoglobin causes a 21% suppression of the direct bilirubin value. According to Michaelsson, the average hemoglobin concentration in samples obtained by a heel stick is about 1.2 g/L and it is not unusual to see hemoglobin levels of 3 g/L. The fact that the ascorbic acid fails to counteract the effect of hemoglobin indicates that bilirubin or azobilirubin is being destroyed before ascorbic acid is added.

The mechanism of hemoglobin interference appears to be as follows: At an acid pH, hemoglobin is oxidized to hematin and, $H_2O_2$ or some form of peroxide is released during the reaction. The peroxide in the presence of heme protein, which acts as a pseudo-peroxidase, oxidizes conjugated bilirubin to a diazo-negative compound. Any unoxidized bilirubin reacts upon addition of the diazo reagent to give the azopigment and no further destruction of the azopigment occurs. It is highly probable that the oxidation product of conjugated bilirubin is conjugated biliverdin.

SUMMARY OF THE PRESENT INVENTION

It is an object of the present invention to disclose a bilirubin assay in which hemoglobin does not interfere with the results.

It is a further object to provide a faster, more accurate assay for direct bilirubin.

In the method of the present invention, a buffer having a pH of about 4 to about 5 and preferably containing a small amount of iodide ion is used instead of the acid diluent in the Michaelsson modification of the Jendrassik-Grof procedure. The preferred buffer is a sodium acetate buffer having a pH of about 4.75 and containing 8 grams per liter of potassium iodide.

The hemoglobin interference in the method of the present invention is negligible. The use of the buffer in place of the acid diluent decreases the rate of the oxidation of hemoglobin to methemoglobin and the iodide ions prevent conjugated bilirubin from being oxidized to biliverdin. As a result, the volume of the diazo reagent may be decreased because the oxidation of hemoglobin and the contribution of unconjugated bilirubin in the direct reaction are dependent upon the diazo concentration. In addition, the incubation time can be decreased from about 10 minutes to about 4 minutes because at a pH of 4.75 the conjugated bilirubin reacts much faster than at the acid pH of 1.5, and the same is true of unconjugated bilirubin.

It will be apparent from the description which follows that objects and advantages, in addition to those described above, may be obtained by the practice of the present invention.

PREFERRED EMBODIMENT OF THE INVENTION

In the preferred practice of the present invention, a 0.5 ml. serum sample containing bilirubin is diluted with about 2.0 ml. of a 0.4 M sodium acetate buffer having a pH of about 4 to about 5 (preferably about 4.75), which contains from 3 to 30 g (preferably 8 grams per liter) of potassium iodide and 0.5 ml. of a diazo reagent is added which contains about 0.9 mmoles per liter to about 2.8 mmoles (preferably 1.8 mmoles) per liter of sodium nitrite in sulfanilic acid solution. The mixture is incubated for about 3 to 10 minutes, preferably 4 minutes, and then there is added 0.2 ml. of an ascorbic acid solution, followed immediately by 3.0 ml. of an alkaline tartrate solution and 2.0 ml. of caffeine reagent. The optimal temperature range is about 20° C. to about 30° C. The absorbance of the sample at 600 nm is then read using a spectrophotometer with a control blank in which sulfanilic acid is used in place of the diazo reagent at zero absorbance.

The concentration of direct bilirubin is calculated by comparison to the absorbance of unconjugated bilirubin standard(s) analyzed by a method for total bilirubin. This is done by adding the bilirubin standard(s) to caffeine reagent instead of acetate buffer and adding the latter at the end (after the alkaline tartrate).

The reagents used in the method of the present invention are the following:

1. Caffeine mixture. Add 50 g. of caffeine, purified alkaloid $C_{18}H_{10}N_4O_2$, 75 g. of sodium benzoate, $C_6H_5COONa$ (USP), and 125 g. of sodium acetate, granular $CH_3COONa.3H_2O$, to distilled water at 50° to 60° C. and bring to 1 liter when cool. The reagent is stable for at least 6 months at room temperature when stored in glass or polyethylene bottles.

2. Diazo I. Add 5.0 g. of sulfanilic acid, $C_6H_4NH_2SO_3H.H_2O$, and 15.0 ml. of concentrated hydrochloric acid, to distilled water and bring to 1 liter. The reagent is stable for at least 6 months at room temperature when stored in glass or polyethylene bottles.

3. Diazo II. Add 500 mg. of sodium nitrite, $NaNO_2$, to distilled water and bring to 100 ml. This reagent is stable up to 2 weeks at 4° to 6° C.

4. Diazo reagent. Mix 10.0 ml. of Diazo I with 0.25 ml. of Diazo II. Use the reagent within 30 minutes of preparation.

5. Alkaline Tartrate. Add 75 g. of sodium hydroxide, NaOH, and 325 g. of potassium sodium tartrate, $KNaC_4H_4O_6.4H_2O$, to distilled water and dilute to 1 liter. This solution is stable for at least 6 months at room temperature when stored in glass or polyethylene bottles.

6. Ascorbic Acid Solution. Dissolve 5 grams of ascorbic acid in 100 ml of distilled water.

7. Sodium Acetate Buffer (pH 4.75). Mix equal volumes 0.4 mol/L sodium acetate and 0.4 mol/L acetic acid. The pH should be 4.75. If not, adjust to 4.75 by adding either 0.4 mol/L sodium acetate or 0.4 mol/L acetic acid. Dissolve 8 grams of potassium iodide per liter of acetate buffer.

It will be appreciated by those skilled in the art that other reagents that function in an acceptable manner may be substituted for those described above. For example, other buffers may be employed in place of the sodium acetate buffer if they provide the desired pH range and other sources of iodide ion may be used in place of potassium iodide.

The reagents used in the method of the present invention may be conveniently supplied in the form of a kit along with the necessary container and instructions.

The absorbence is read at 600 nm using a spectrophotometer such as a Gilford 300N, a Cary 210 or the like. The results obtained are linear up to 110 mg/l of conjugated bilirubin.

The method of present invention may be used to evaluate the bilirubin content in serum or other body fluids. Preferably serum or heparinized plasama is employed.

A comparison of patient specimens by both the previous methods (Michaelsson, supra. and Doumas et al. Clin. Chem. 28/11, 2305–2308 (1982)), and the faster method of the present invention showed that the results obtained by the two methods were in good agreement.

With the method of the present invention, conjugates of bilirubin with taurine react quantitatively, that is, values for direct bilirubin are identical to total bilirubin; with the previous methods (Michaelsson and Doumas et al. supra.) direct bilirubin values are about 90% of total bilirubin.

Naturally occurring bilirubin conjugates, consisting of mono- and diglucuronide, do not react quantitatively with either method. This is not surprising because, in addition to the mono- and diconjugates, these preparations contain a variety of acyl isomers as well as conjugates with xylose and glucose, which may exhibit different reactivities in the direct reaction.

It will be apparent to those skilled in the art that a number of modifications may be made without departing from the spirit and scope of the present invention.

We claim:

1. A method of measuring direct bilirubin in a sample which comprises forming a mixture of the sample and a buffer having a pH of about 4 to 5 which contains iodide ions to both decrease the oxidation of hemoglobin to methemoglobin and to prevent conjugated bilirubin from being oxidized to biliverdin, adding to the mixture a diazo reagent which contains about 0.9 mmoles to about 2.8 mmoles per liter of sodium nitrate in sulfanilic acid, incubating the resulting mixture for about 4 minutes, adding sequentially ascorbic acid, alkaline tartrate and a caffeine reagent and then reading the absorbance which indicates the quantity of direct bilirubin present.

2. A method of claim 1 in which the buffer solution is a sodium acetate buffer having a pH of about 4.75 which contains about 8 grams per liter of potassium iodide.

3. In the method of measuring direct bilirubin in a sample of body fluid which comprises adding to the sample an acid reagent to prevent unconjugated bilirubin in the sample from reacting, adding diazo reagent, incubating the resulting mixture, then sequentially adding ascorbic acid to destroy excess diazo reagent and caffeine reagent to prevent overestimation of the direct bilirubin and then reading the absorbance of the mixture with a spectrophotometer which indicates the quantity of direct bilirubin present, the improvement which comprises employing as the acid diluent a buffer having a pH of about 4 to 5 which contains iodide ions effective to prevent conjugated bilirubin from being oxidized to biliverdin, and then incubating the mixture for about 4 minutes.

* * * * *